US007666448B2

(12) United States Patent
Mower

(10) Patent No.: US 7,666,448 B2
(45) Date of Patent: *Feb. 23, 2010

(54) SKIN CLEANSING ARTICLE

(75) Inventor: Thomas E. Mower, Payson, UT (US)

(73) Assignee: Sakura Properties, LLC, Springville, UT (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/307,034

(22) Filed: Jan. 19, 2006

(65) Prior Publication Data
US 2006/0210517 A1 Sep. 21, 2006

Related U.S. Application Data

(63) Continuation-in-part of application No. 11/083,826, filed on Mar. 18, 2005.

(51) Int. Cl.
A01N 65/00 (2009.01)
(52) U.S. Cl. ..................................... 424/725
(58) Field of Classification Search .......... None
See application file for complete search history.

(56) References Cited

U.S. PATENT DOCUMENTS

| 1,607,844 | A | 11/1926 | Neilsen |
| 1,687,625 | A | 10/1928 | Mackenzie |
| 2,933,431 | A | 4/1960 | Sperouleas |
| 3,240,775 | A | 3/1966 | Schweiger |
| 3,264,188 | A | 8/1966 | Gresham |
| 3,301,746 | A | 1/1967 | Sanford |
| 3,697,287 | A | 10/1972 | Wintz |
| 3,700,623 | A | 10/1972 | Keim |
| 3,741,273 | A | 6/1973 | Meade |
| 3,772,076 | A | 11/1973 | Keim |
| 3,911,105 | A | 10/1975 | Papantoniou et al. |
| 4,009,313 | A | 2/1977 | Crawford |
| 4,112,167 | A | 9/1978 | Dake |
| 4,139,619 | A | 2/1979 | Chidsey |
| 4,481,243 | A | 11/1984 | Allen |
| 4,556,560 | A | 12/1985 | Buckingham |
| 4,596,812 | A | 6/1986 | Chidsey |
| 4,670,285 | A | 6/1987 | Clandinin |
| 4,698,360 | A | 10/1987 | Masquelier |
| 4,871,550 | A | 10/1989 | Millman |
| 4,996,044 | A | 2/1991 | Mercado |
| 4,996,238 | A | 2/1991 | Matravers |
| 5,021,245 | A | 6/1991 | Borschel |
| 5,059,686 | A | 10/1991 | Sau |
| 5,152,983 | A | 10/1992 | Nambudiry |
| 5,165,933 | A | 11/1992 | Oishi |
| 5,292,538 | A | 3/1994 | Paul |
| 5,362,488 | A | 11/1994 | Sibley |
| 5,397,786 | A | 3/1995 | Simone |
| 5,409,703 | A | 4/1995 | McAnalley |
| 5,415,879 | A | 5/1995 | Oh |
| 5,541,166 | A | 7/1996 | Parish et al. |
| 5,631,032 | A | 5/1997 | Gil |
| 5,672,339 | A | 9/1997 | Soyama et al. |
| 5,700,590 | A | 12/1997 | Masor |
| 5,720,966 | A | 2/1998 | Ostendorf |
| 5,733,572 | A | 3/1998 | Unger |
| 5,762,945 | A | 6/1998 | Ashley |
| 5,776,494 | A | 7/1998 | Guskey |
| 5,814,188 | A | 9/1998 | Vinson |
| 5,834,044 | A | 11/1998 | Schmitz |
| 5,861,048 | A | 1/1999 | Kamasaka |
| 5,871,550 | A | 2/1999 | Goedegebuur et al. |
| 5,891,888 | A | 4/1999 | Strahl |
| 5,935,556 | A * | 8/1999 | Tanner et al. ............ 424/59 |
| 5,980,922 | A | 11/1999 | Mackey |
| 6,033,887 | A | 3/2000 | Champagne |
| 6,051,235 | A | 4/2000 | Theuer |
| 6,051,236 | A | 4/2000 | Portman |
| 6,077,557 | A | 6/2000 | Gordon et al. |
| 6,190,724 | B1 | 2/2001 | Sawatzki et al. |
| 6,268,182 | B1 | 7/2001 | Kamasaka |
| 6,346,237 | B2 | 2/2002 | Lemann |
| 6,447,817 | B1 | 9/2002 | Niyiro |
| 6,517,849 | B1 | 2/2003 | Seger |
| 6,521,240 | B1 | 2/2003 | Minerath |
| 6,573,250 | B2 | 6/2003 | Umeda |

(Continued)

FOREIGN PATENT DOCUMENTS

EP 1199942 5/2002

(Continued)

OTHER PUBLICATIONS

Bank, Ginny and Schauss, Alex, Antioxidant Testing; an ORAC Update. www.nutraceuticalsworld.com, Mar. 2004.

(Continued)

Primary Examiner—Michael V Meller
(74) Attorney, Agent, or Firm—Clayton, Howarth & Cannon, P.C.

(57) ABSTRACT

A skin care article including a carrier and a moist application that includes partially hydrolyzed fucoidan. The partially hydrolyzed fucoidan may by sulfonated. The present invention also discloses a method of making a skin care article by partially hydrolyzing fucoidan, mixing it with a base and applying it to a carrier. The carrier may be flushable.

5 Claims, No Drawings

U.S. PATENT DOCUMENTS

| | | |
|---|---|---|
| 6,589,537 B2 | 7/2003 | Harbeck |
| 6,602,869 B1 | 8/2003 | Galey |
| 6,616,950 B2 | 9/2003 | Pushpangadan |
| 6,641,848 B1 | 11/2003 | Bonte |
| 6,656,903 B1 | 12/2003 | Sawatzki |
| 6,673,755 B2 | 1/2004 | Wei |
| 6,693,209 B2 | 2/2004 | Van Es et al. |
| 6,703,027 B2 | 3/2004 | Kurosawa |
| 6,730,333 B1 | 5/2004 | Garrity |
| 6,812,220 B2 | 11/2004 | Jackson et al. |
| 6,863,918 B2 | 3/2005 | Bindels |
| 6,890,543 B2 | 5/2005 | Minami |
| 6,896,766 B2 | 5/2005 | Sarbo |
| 2002/0076431 A1 | 6/2002 | Umeda |
| 2002/0197352 A1 | 12/2002 | Portman |
| 2003/0039670 A1* | 2/2003 | Mizutani et al. ............ 424/401 |
| 2003/0045572 A1 | 3/2003 | Niyiro |
| 2003/0064958 A1 | 4/2003 | Jackson et al. |
| 2003/0083209 A1 | 5/2003 | Moodycliffe |
| 2003/0207004 A1 | 11/2003 | Theuer |
| 2004/0043961 A1 | 3/2004 | Wu |
| 2004/0077523 A1 | 4/2004 | Ochiai et al. |
| 2004/0180850 A1 | 9/2004 | Natunen |
| 2004/0242665 A1 | 12/2004 | Boulle |
| 2005/0013871 A1 | 1/2005 | Niazi |
| 2005/0015854 A1 | 1/2005 | Eisenberg |
| 2005/0019356 A1 | 1/2005 | Bissett |
| 2005/0053713 A1 | 3/2005 | Birch |
| 2005/0058672 A1 | 3/2005 | Gupta |
| 2005/0058674 A1 | 3/2005 | Joseph |
| 2005/0058833 A1 | 3/2005 | Krzysik |
| 2005/0064070 A1 | 3/2005 | Liebrecht |
| 2005/0095260 A1 | 5/2005 | Pardoe |
| 2005/0095320 A1 | 5/2005 | Botteri |
| 2005/0096295 A1 | 5/2005 | McMahon |
| 2005/0100636 A1 | 5/2005 | Botteri |
| 2005/0129708 A1 | 6/2005 | Fuji et al. |
| 2005/0137175 A1 | 6/2005 | Bernard |
| 2005/0142084 A1* | 6/2005 | Ganguly et al. ............... 424/63 |
| 2005/0147732 A1 | 7/2005 | Schwach-Abdellaoui |
| 2005/0191405 A1 | 9/2005 | Okos |
| 2005/0192218 A1 | 9/2005 | Ellis |
| 2005/0214332 A1 | 9/2005 | Osborne |
| 2005/0214383 A1 | 9/2005 | Bubnis |
| 2005/0220828 A1 | 10/2005 | Ullom |
| 2005/0230069 A1 | 10/2005 | Hilbig |
| 2005/0232876 A1 | 10/2005 | Minga |
| 2005/0239749 A1 | 10/2005 | Kambayashi |
| 2005/0244369 A1 | 11/2005 | Georgiades |
| 2006/0292255 A1* | 12/2006 | Moffett et al. .............. 424/769 |

FOREIGN PATENT DOCUMENTS

| | | |
|---|---|---|
| EP | 0846422 | 5/2003 |
| JP | 3225923 | 8/2001 |

OTHER PUBLICATIONS

Oliver Starr, Tumeric Phytonutrient Protection for a Variety of Physiological Stresses, VRPs Nutritional News, May/Jun. 1996.

Marilyn Sterling, Proanthocyanidin Power, Nutrition Science News, Jun. 2000.

High-ORAC Foods May SLow Aging, Agricultural Research, Feb. 2005.

Substituting Isosorbides for Phthalates, yet2.com, Dec. 2004.

Novel Plasticizers to Replace Phthalates in PVC or Other Plastics, yet2.com, http://www.yet2.com/app/list/techpak?id=33822&sid=20&abc=0.

Hwan Su Yoon, Ju Yeo Lee, Sung Min Boo, Debashish Bhattacharya, Phylogny of Alariaceae, Laminariaceae, and Lesoniaceae (RuBisCo Spacer and Nuclear-Encoded ITS Sequence Comparisons, Molecular Phylogenitics and Evolution, Nov. 2001, vol. 21, No. 2, pp. 231-243.

Sakait, Ishizukak., Kato, I, Isolation and Characterization of a Fucoidan-Degrading Marine Bacterium, Mar Biotechnical, Sep.-Oct. 2003.

Rita Elkins, Prize Sea Plant of Tonga and the South Pacific—Limu Moui, 2001.

Berteua, Oliver and Mulloy, Barbara, Sulfonated fucans, fresh perspectives; structures, funtions, and biological properties of sulfated fucans and an overview of enzymes active toward this class of polysaccharide, Glycobiology, 2003, vol. 13, No. 6.

Del Bigio, Mr. Yan HJ, Campbell, TM, Peeling, J., Effect of Fucoian Treatment on Collagenase-induced Intracerebral Hemorrhage in rats, 2002 Annual Mtg. and Food Expo., Anaheim, CA.

Shibata, H., Imuro, M., Uhiya, N., Kawamori, T., Nagaoka, M., Yeyama S., Hashimoto S., Yokokura T., Sugimura T., Wakabiashi K., Preventive Effects of Cladosiphon Fucoidan Against *Helicobacter pylori* Infection in Mongolian Gerbils, PubMed, Feb. 2003.

A.I., Usov, G.P. Smrinova, N. G. Klochkova, Polysaccharides of Algae; Polysaccharide Composition of Several Brown Algae From Kamchatka, 27 Russian Journal of Bioorganic Chemistry, vol. 27, No. 6, pp. 395-399, 2001.

Berangere, Tissot, Regis, Daniel, Biological Properties of Sulfated Fucans; the Potent Inhibiting Activity of Algal Fucoidan Against the Human Complement System, Glycobiology, 2003 vol. 13, No. 12.

Matou S., Helley D., Chabut D, Bros A Fischer AM, Effect of Fucoidan on Fibroblast Growth Factor-2 induced Angiogenesis in Vitro Elsevier Science, May 15, 2002.

Takara-Takara Kombu Fucoidan (Functional Seaweed Dietary Fiber).

Soeda S, Kozako T. Iwata K., Himeno H., Oversulfated Fucoidan Inhibits the Basic Fibroblast Growth Factor-induced Tube Formation by Human Umbilical Vein Endothelial Cells; Its Possible Mechanism of Action, Department of Biochemistry, Faculty of Pharmaceutical Sciences, Fukuoka University, Jun. 2, 2002.

A Guide to the Seaweed Industry, FAO Fisheries Technical Paper 441, 2003.

Herworld-Back to Basics—http://www.herworld.com/Beauty_report.html.

Desitin—http://www.desitin.com/en/?dsp=21&psp=20.

Desitin Creamy—http://www.desitin.com/en/?dsp=22&psp=20.

Boudreauxs Butt Paste—http://www.skinstore.com/store/product.asp?catID=422&prodID=514.

Johnson's Baby Oil—http://www.johnsonsbaby.com/products/oil/baby-oil.

Johnson's Creamy Baby Oil—http://www.johnsonsbaby.com/products/oil/creamy-baby-oil.

Johnson' Baby Oil Gel with Aloe Vera and Vitamin E—http://www.johnsonsbaby.com/products/oil/baby-oil-with-aloe.

Pediatric Products Similac Advance—http://rpdcon40.ross.com/pn/PediatricProducts.NSF/0/706d4b6080c6E7C085256BA30052E1D1?OpenDocument.

Marquardt, Thorsten; Luhn, Kerstin; Srikrishna, Geetha; Freeze, Hudson H; Harms, Erik; Vestweber, Dietmar. Correction of Lukocyte Adhesion Deficiency Type II With Oral Fucose-Blood vol. 94, No. 12, (Dec. 15, 1999) pp. 3976-3985.

Russian Adaptogens: Health Secrets Revealed—http://members.tripod.com/macyuen-ivil/id13.html (Dec. 2004).

Polysaccharide Found in the Seaweed Kombu, U-Foucoidan, Discovered to Cause Cancer Cells to self Destruct (Jun. 17, 1996).

\* cited by examiner

SKIN CLEANSING ARTICLE

BACKGROUND OF THE INVENTION

This application is a Continuation-in-Part of, and claims the benefit of application Ser. No. 11/083,826, filed on 18 Mar. 2005, by Thomas E. Mower, entitled Fucoidan Compositions and Methods for Dietary and Nutritional Supplements, the entirety of which is herein incorporated by reference.

FIELD OF THE INVENTION

The present invention relates to skin cleansing articles, specifically skin cleansing articles for the cleansing and healing of the skin.

DESCRIPTION OF THE RELATED ART

Skin can be affected by several of the environmental conditions to which it is exposed. One way of protecting skin is to clean it of the conditions that negatively affect it. For example, when skin is exposed to human secretions, such as sweat, urine, feces, mucous, and so forth, the secretion may irritate the skin unless it is cleaned from the skin. Alternatively, dirt, pollen, pathogens, and so forth may collect on the skin and damage the skin. One way to stop such irritation and damage is to clean the substance from the skin. However, simply cleaning the skin of the irritants may not suffice to promote healing of the skin.

In particular, skin areas that may be repeatedly exposed to such bodily fluids may be further damaged. For example, persons who wear diapers, adsorptive underwear, and the like may have areas of skin that are exposed to such bodily fluids for extended periods of time. Though diapers may be changed often, infants who wear diapers may have areas of skin that are exposed to urine, sweat, feces, and so forth for extended periods of time. As such, these persons may experience extensive skin damage over these areas of the skin. In another example, persons who are unable to bathe for extended periods of time may experience long periods of exposure of skin to certain bodily fluids. Soldiers, for example, may be required to work for several days without bathing, thus exposing their skin to sweat, oils, and so forth for these long periods.

A further detriment to these types of situations is the possible chaffing that may occur when the bodily fluid is held next to the skin by an article such as clothing, a diaper, adsorptive underwear, and so forth. For example, a toddler that wears a diaper may experience chaffing because of the rubbing of the diaper on the skin that is exposed to feces, urine, sweat, or the like during movement.

Failure to remove fecal matter from the anal area can have a deleterious effect on personal hygiene. The fecal matter remaining on the skin after post-defecation cleansing has a high bacterial and viral content, is malodorous and is generally dehydrated. These characteristics increase the likelihood of perianal disorders and personal discomfort (e.g., itching, irritation, chafing, etc.). Further, the residual fecal matter stains undergarments and causes unpleasant odors to emanate from the anal region. Thus, the consequences of inadequate perianal cleansing are clearly unattractive. One specific detriment of failure to remove fecal matter includes diaper rash.

Diaper rash is an irritation of the skin when human waste products such as feces or urine is held next to the skin for periods of time. Diaper rash is commonly caused when a person wears a soiled diaper that holds the waste product next to the skin. Diaper rashes can occur not only in infants and toddlers who wear diapers because they have not yet been toilet trained, but also may occur in young children who wear diapers, children, youth, and adults who must wear a diaper for particular reasons, or any who must wear an article that keeps human waste products next to their skin. For example, many of the elderly loose control of their bladder, or digress to a state in which they cannot use a toilet, and must wear diapers. Hospitalized, incapacitated, or handicapped individuals may be forced to wear articles that trap human waste products next to their skin, if even for a short period of time. However, while it is known that body waste "causes" diaper rash, the precise component or components of the urine or feces which are responsible for the resulting irritation of the skin remain the subject of much controversy. The most commonly accepted list of factors linked to diaper rash includes ammonia, bacteria, the products of bacteria action, urine pH, *Candida albicans*, and moisture. This condition is also referred to as diaper dermatitis, napkin dermatitis, napkin rash, and nappy rash.

Reference to diapers in this document should be read to include any article that holds human waste products to the skin, whether this be the purpose of the article or not. For example, diapers may include diapers, underwear, absorbent pads or articles, incontinence articles, and so forth.

Among infants, diaper rash may be a relatively common ailment. Most parents can attest to at least one instance when their infant or child has had a diaper rash.

While no true causative agent has been identified, a diverse range of factors have been suspected of being associated with diaper rash and diaper dermatitis. Because these suspected agents all possess diverse properties and require such varied therapies, conventional methods of treatment for diaper dermatitis have been directed toward a straightforward attempt to minimize the contact of the skin with the feces or urine present in a soiled diaper. An artificial barrier is usually provided between the skin and the body waste to accomplish this. There have also been further attempts directed toward counteracting other suspected causes of diaper rash by promoting dryness in the diapered area, and preventing microbial growth and inflammation with conventional agents. Such a strategy would include frequent diaper changing, reduced use of plastic pants, triple diapering, careful washing and sterilization of diapers, treatment with an anti-Candidal agent, reduction of inflammation (by application of a topical application of a low potency glucocorticoid steroid), and the possible use of a bacteriostatic agent as a prophylactic measure in the diaper rinse. However, because the exact components of urine or feces which act as factors or cofactors contributing to diaper dermatitis have never been precisely identified, the most effective method of treating diaper dermatitis to date has been the artificial barrier. This had led to the frequent use of an occlusive, barrier-type topical, such as petrolatum or zinc oxide, to provide this protection, preventing the unknown offending component from coming in contact with the skin.

For example, one ointment sold under the tradename Desitin®, (Leeming Division of Pfizer, Inc.) is probably the most common topical used in treating diaper rash. It contains both of the common barrier materials (zinc oxide and petrolatum) and additionally contains two common skin conditioning agents (cod liver oil and lanolin). All of these agents are commonly used in topical skin conditioning preparations.

Another commonly used ointment is sold under the tradename Butt Paste® (Boudreaux's Family Pharmacy, Inc., Covington, La.). As with Desitin®, Butt Paste® includes the barrier materials of zinc oxide and petrolatum. Butt Paste® also contains barrier ingredients mineral oil and white wax.

As skin conditioning agents, Butt Paste® includes peruvian balsam and castor oil. Butt Paste® further includes castor oil.

Petrolatums, as well as zinc oxide, are well known to be highly effective barrier materials.

Zinc oxide is also known to be effective when applied externally—as a mild astringent for the skin, as a barrier material to prevent eczema, and also as a barrier protective to slight excoriations. It has been used in pastes and cremes in combination with many other topical actives. Zinc oxide is almost totally insoluble in water.

Petrolatum (petroleum jelly; paraffin jelly; vasoliment) is commonly used as an occlusive barrier material in topical preparations. Petrolatum is a purified mixture of semi-solid hydrocarbons of the general formula $C_nH_{2n+2}$, when n is about 16 to about 32. Premium petrolatum is a white, semi-solid, unctious mass which is odorless and tasteless. It is a product of commerce.

In one example of a patented diaper rash ointment, Buckingham discloses in U.S. Pat. No. 4,556,560 methods for the treatment and prevention of diaper rash and diaper dermatitis caused by the prolonged contact of human skin with body waste. The methods of the present invention employ the topical application of a minimum inhibitory concentration of a pharmaceutically-acceptable lipase-inhibiting agent to the area in need of such treatment, or the area where prevention is desired. The lipase-inhibiting agent may be a water-soluble metallic salt, such as $ZnCl_2$, and may be applied in combination with a barrier-like application. The effectiveness of these methods is surprising in light of the present confusion and controversy surrounding the actual causes of diaper rash, and the heretofore unrecognized role of lipase as a factor in the cause of diaper rash and diaper dermatitis.

In a further example, Matravers discloses in U.S. Pat. No. 4,996,238 a skin protective composition for exhibiting enhanced water repellency and conditioning effects containing aliphatic waxes and hydrophobic silicones in a nonallergenic, non-toxic, cosmetically acceptable carrier. The composition is useful to protect mammals from solar radiation and in the treatment of diaper rash. The composition includes a base containing a synthetic aliphatic wax, that is, a high molecular weight $C_{18}$-$C_{36}$ saturated synthetic wax fatty acid admixed with one or more hydrophobic silicones, anhydrous hydrophobic silicone, and a pharmacologically acceptable carrier.

The skin is made up of two major layers. The epidermis is the top layer and forms a protective covering for skin and controls the flow of water and substances in and out of the skin. To stay healthy, the skin has to cope with changing environmental conditions and repair damage at the same time. The skin is in a constant state of repair as it sheds the dead cells on the surface and replenishes the lower layers. The dermis is the lower level of the skin and is the layer that provides the strength, elasticity, and thickness to the skin. Cells in the dermis are responsible for synthesis and secretion of all the dermal matrix components, such as collagen, elastin, and glycosaminoglycans. Collagen provides the strength, elastin the elasticity, and glycosaminoglycans the moistness and plumpness of the skin.

Skin may be abused by soaps, emulsifier-based cosmetics, hot water, organic solvents, and even substances that may be expelled from the body such as oils, sweat, urine, feces, tears, blood, and so forth. These each contribute to rob skin of essential moisture, and to create a stressed barrier that does not function properly. Moisture loss and irritation increases, leaving skin sensitive, scaly, and dry. Free-radical activity multiplies, causing more wrinkles and premature aging.

Furthermore, the skin is subject to deterioration through dermatological disorders, environmental abuse, such as from wind, air conditioning, and central heating, or through the normal aging process, which may be accelerated by exposure of skin to sun. The thickness of the dermal layer is reduced due to aging, thus causing the skin to slacken. This is believed to be partially responsible for the formation of wrinkles. In recent years, the demand for cosmetic compositions and cosmetic methods for improving the appearance and condition of skin has grown enormously.

Conventional toilet tissue products used for anal cleaning are essentially dry, low density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil-soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, causing it to adhere more tenaciously to the perianal skin and hair and making its removal difficult in the extreme. Pressing the tissue forcefully against the perianal skin will remove more of the fecal matter but is intensely painful for people suffering from anal disorders and can excoriate even normal perianal skin, potentially causing irritation, inflammation, pain, bleeding, and infection.

To improve perianal cleaning, wipes have been developed that are kept in a dispenser and are typically soaked in a reservoir of a moistening solution. Examples of such products include wipes that are often used to clean babies after bowel movements and can have other additives in the moistening solution to soothe the skin. These wipes can have permanent wet strength such that they are not flushable. Also, these prior wipes are often too wet to dry the skin and tend to have a "cold" feel. There is also a lack of consistency in terms of the moisture content of each of the wipes.

Moistenable dry tissue products have also been used in perianal cleaning. These moistenable tissue products usually have temporary wet strength such that they are flushable. However, the users of these products have to separately wet the tissue, which can be inconvenient. It is also difficult to get the desired moisture level with such products. Also, the temporary wet strength of such products is typically inadequate and needs to be improved.

Art in the area of skin cleansing articles also includes several patents describing articles and their method of manufacture. For example, U.S. Pat. No. 1,687,625 to Mackenzie discloses a composition of matter that has for one object a convenient and portable form of a normally plastic medium used for toilet or medical purposes.

In a further example, in U.S. Pat. No. 3,264,188, Gresham discloses a sanitary impregnated skin wiper. More specifically it relates to an impregnated tissue of improved softness especially designated for proctological use of for use by persons suffering from anorectal disorders.

In yet another example, Dake, in U.S. Pat. No. 4,112,167, discloses an article of manufacture for cleansing the skin with improved effectiveness. A soft, flexible web having a low density wiping zone works in concert with a lipophilic cleansing emollient to remove soil from the skin with improved effectiveness. The lipophilic cleansing emollient reduces dehydration of the soil and weakens the soil-skin adhesive forces while the low density wiping zone of the web entraps and thus removes the soil from the skin.

In a final example, Mackey discloses in U.S. Pat. No. 5,980,922 articles useful in cleansing, and particularly to wet-like cleansing wipes that are especially useful for hard surface cleaning, and in personal cleansing such as baby wipes and particularly for removal of perianal soils. These articles comprise: a carrier; and an emulsion applied to the carrier. The emulsion comprises (1) from about 2 to about 60% of a continuous solidified lipid phase comprising a waxy lipid material having a melting point of about 30° C. or higher, (2) from about 39 to about 97% of an internal polar (e.g., water) phase dispersed in the lipid phase; (3) an effective amount of a non-silicon containing emulsifier, where the emulsifier has a viscosity at 55° C. of greater than about 500 centipoise; and (4) and an optional second emulsifier having a viscosity at 55° C. of less than about 400 centipoise. Because the emulsion comprises a waxy external phase, the internal polar phase is retained in the emulsion until in-use shear pressures break the emulsion, thereby providing desired moisture for cleaning. The invention also relates to a process for making the cleaning articles.

Consumer demand for natural-based products has been growing in recent years. Chemical synthesis is perceived as environmentally unsafe. A chemically synthesized ingredient may contain harsh chemicals. Natural products are perceived as more pure and mild, and thus superior to chemically synthesized products. Delivering a cosmetic benefit from plant sources, however, is not trivial. To derive a real benefit from a natural source, not only does a plant or a part of the plant containing a specific active ingredient have to be identified, but a minimum concentration and/or a specific extract of that plant has to be identified that truly delivers a cosmetic benefit.

Accordingly, consumers demand an effective skin cleansing article for the skin and wrinkles that moisturizes, heals, and soothes the vulnerable and delicate surface of the skin. Further, consumers demand that treatment for the skin be based on natural products to promote healing and preserve youthful appearance.

Fucoidan is a sulfated polysaccharide found in many sea plants and animals and is particularly concentrated in the cell walls of brown algae (*Phaeophyceae*). Fucoidan is a complex carbohydrate polymer composed mostly of sulfated L-fucose residues. These polysaccharides are easily extracted from the cell wall of brown algae with hot water or dilute acid and may account for more than 40% of the dry weight of isolated cell walls. O. Berteau & B. Mulloy, *Sulfated Fucans, Fresh Perspectives: Structures, Functions, and Biological Properties of Sulfated Fucans and an Overview of Enzymes Active Toward this Class of Polysaccharide*, 13 *Glycobiology* 29R-40R (2003). Fucoidan structure appears to be linked to algal species, but there is insufficient evidence to establish any systematic correspondence between structure and algal order. High amounts of α(1-3) and α(1-4) glycosidic bonds occur in fucoidans from *Ascophyllum nodosum*. A disaccharide repeating unit of alternating α(1-3) and α(1-4) bonds represents the most abundant structural feature of fucoidans from both *A. nodosum* and *Fucus vesiculosus*, which are species of seaweed. Sulfate residues are found mainly in position 4. Further heterogeneity is added by the presence of acetyl groups coupled to oxygen atoms and branches, which are present in all the plant fucoidans. Following is a representation of *A. nodosum* fucoidan:

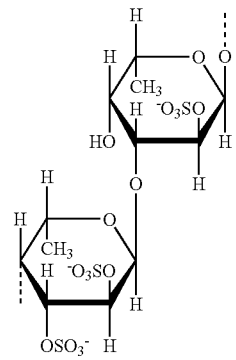

Fucoidan-containing seaweeds have been eaten and used medicinally for at least 3000 years in Tonga and at least 2000 years in China. An enormous amount of research has been reported in the modern scientific literature, where more than 500 studies are referenced in a PubMed search for fucoidan.

The physiological properties of fucoidans in the algae appear to be a role in cell wall organization and possibly in cross-linking of alginate and cellulose and morphogenesis of algal embryos. Fucoidans also have a wide spectrum of activity in biological systems. They have anticoagulant and anti-thrombotic activity, act on the inflammation and immune systems, have antiproliferative and antiadhesive effects on cells, and have been found to protect cells from viral infection.

Further, fucoidan has numerous beneficial functions that heal and strengthen different systems of the body, including anti-viral, anti-inflammatory, anti-coagulant, and anti-tumor properties. A. I. Usov et al., *Polysaccharides of Algae: Polysaccharide Composition of Several Brown Algae from Kamchatka*, 27 *Russian J. Bio. Chem.* 395-399 (2001). Fucoidan has been found to build and stimulate the immune system. Research has also indicated that fucoidan reduces allergies, inhibits blood clotting, fights diabetes by controlling blood sugar, prevents ulcers, relieves stomach disorders, reduces inflammation, protects the kidneys by increasing renal blood flow, and detoxifies the body. Fucoidan also helps to reduce and prevent cardiovascular disease by lowering high cholesterol levels and activating enzymes involved in the beta-oxidation of fatty acids.

A Japanese study found that fucoidans enhanced phagocytosis, the process in which white blood cells engulf, kill, digest, and eliminate debris, viruses, and bacteria. An American study reported that fucoidans increased the number of circulating mature white blood cells. An Argentine study and a Japanese study found that fucoidans inhibited viruses, such as herpes simplex type I, from attaching to, penetrating, and replicating in host cells. A Swedish study is among the many that showed fucoidans inhibit inflammation cascades and tissue damage that may lead to allergies. Other studies, such as one in Canada, found that fucoidans block the complement activation process that is believed to play an adverse role in chronic degenerative diseases, such as atherosclerosis, heart attack, and Alzheimer's disease. Two American studies found that fucoidans increase and mobilize stem cells.

Researchers have also determined that fucoidan tends to combat cancer by reducing angiogenesis (blood vessel growth), inhibiting metastasis (spreading of cancer cells to other parts of the body), and promoting death of cancer cells. Certain societies that make brown seaweed part of their diet appear to have remarkably low instances of cancer. For example, the cancer death rate in Okinawa is the lowest of all the prefectures in Japan. It is noteworthy that the prefecture of Okinawa, where the inhabitants enjoy some of the highest life expectancies in Japan, also happens to have one of the highest per capita consumption rates of fucoidans.

Brown seaweed, a ready source of fucoidan, is found in abundance in various ocean areas of the world. One of the best locations that provides some of the highest yields of fucoidan is in the clear waters surrounding the Tongan islands, where the seaweed is called limu moui. In Japan, hoku kombu (*Laminaria japonica*), is said to be particularly rich in fucoidans and is similar to limu moui. The Japanese also consume at least two other types of brown seaweed-wakame and mozuku (*Cladosiphon* and *Nemacystus*).

Typically, about four percent by weight of Tongan limu moui is fucoidan. There are at least three types of fucoidan polymer molecules found in brown seaweed. U-fucoidan, having about 20 percent glucuronic acid, is particularly active in carrying out cancer cell destruction. F-fucoidan, a polymer of mostly sulfated fucose, and G-fucoidan, which includes galactose, both tend to induce the production of HGF cells that assist in restoring and repairing damaged cells. All three types of fucoidan also tend to induce the production of agents that strengthen the immune system.

What is needed is a skin cleansing article that solves one or more of the problems described herein and/or one or more problems that may come to the attention of one skilled in the art upon becoming familiar with this specification. One such problem that is not solved by the cited prior art is the use of a natural component in an article to assist in regeneration, healing, and/or reverses skin damage. Another such problem includes providing an article that assists in anti-aging, regeneration of cells, promoting youthfulness, reducing inflammation, minimizing visible signs of biological and/or environmental aging, and/or fighting free radicals using anti-oxidants.

SUMMARY OF THE INVENTION

The present invention has been developed in response to the present state of the art, and in particular, in response to the problems and needs in the art that have not yet been fully solved by currently available skin cleansing articles. According to one embodiment of the present invention is a skin cleansing article for cleansing and healing of skin including a carrier and a moist application including partially hydrolyzed fucoidan.

The partially hydrolyzed fucoidan may be sulfonated. The partially hydrolyzed fucoidan may be derived from the group consisting of: Japanese mozuku seaweed, Japanese kombu seaweed, Tongan limu moui seaweed, and combinations thereof. The moist application may include from about 10 to about 99 weight percent fucoidan. The moist application may further include a derivative of mangosteen plant. The moist application may further include honey. The skin cleansing article may further include a barrier application. The barrier application may include zinc oxide and partially hydrolyzed fucoidan. The moist application may include an analgesic. The moist application and the barrier application may be on a single surface of the carrier. The carrier may include the barrier application and the moist application in alternating segments.

According to another embodiment of the present invention is a method of making a skin cleansing article, comprising preparing a moist application including partially hydrolyzed fucoidan, by harvesting Tongan limu moui seaweed, removing extraneous material, mixing the Tongan limu moui seaweed with an aqueous buffer while heating, and filtering, and mixing the partially hydrolyzed fucoidan with a base, and applying the moist application to a carrier.

The carrier may comprise a non-woven material. The method may further include the step of sulfonating the partially hydrolyzed fucoidan by addition of sulfuric acid. The moist application may further include a derivative of mangosteen plant. The moist application may further include honey. The method may further include the step of applying a barrier application to the carrier. The barrier application may include zinc oxide and partially hydrolyzed fucoidan. The moist application may include an analgesic. The carrier may be flushable.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

DETAILED DESCRIPTION OF THE INVENTION

For the purposes of promoting an understanding of the principles of the invention, reference will now be made to specific language will be used to describe the specific embodiments of the present invention, and the alternatives. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to "one embodiment," "an embodiment," or similar language means that a particular feature, structure, or characteristic described in connection with the embodiment is included in at least one embodiment of the present invention. Thus, appearances of the phrases "one embodiment," "an embodiment," and similar language throughout this specification may, but do not necessarily, all refer to the same embodiment, different embodiments, or component parts of the same or different illustrated invention. Additionally, reference to the wording "an embodiment," or the like, for two or more features, elements, etc. does not mean that the features are related, dissimilar, the same, etc. The use of the term "an embodiment," or similar wording, is merely a convenient phrase to indicate optional features, which may or may not be part of the invention as claimed.

In describing and claiming the present invention, the following terminology will be used in accordance with the definitions set out below.

As used herein, "comprising," "including," "containing," "is," "are," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "partially hydrolyzed fucoidan" means fucoidan that has been hydrolyzed into smaller polymers and oligomers, but not so thoroughly hydrolyzed as to result in complete hydrolysis to substantially primarily monosaccharides.

As used herein, "lotions" are liquids, often suspensions or dispersions, intended for external application to the body.

As used herein, "creams" are soft preparations. Creams of the oil-in-water (O/W) type include preparations such as foundation creams, hand creams, shaving creams, and the like. Creams of the water-in-oil (W/O) type include cold creams, emollient creams, and the like. Pharmaceutically, creams are solid emulsions containing suspensions or solutions of active ingredients for external application. Generally, preparations of this type are classified as ointments. Specifically, they belong to the emulsion-type bases.

As used herein, "ointments" are semisolid preparations for external application of such consistency that may be readily applied to the skin. They should be of such composition that they soften, but not necessarily melt, when applied to the body. They serve as applications for the topical application of active ingredients and also function as protectives and emollients for the skin. For many years ointments were limited by definition and use to mixtures of fatty substances. Today, in addition to such oleaginous mixtures, there are ointment preparations possessing the same general consistency but entirely free of oleaginous substances. In many instances, they are emulsions of fatty or wax-like materials with comparatively high proportions of water. These emulsions may be either water-in-oil (W/O) or oil-in-water (O/W) emulsions, depending primarily on the selection of the emulsifying agent. Such semisolid emulsions are also referred to as creams. Creams and ointments containing large amounts of insoluble powders are referred to as pastes. Pastes are usually stiffer and more absorptive than creams and ointments.

Each statement of an embodiment is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The independent embodiments are considered to be able to be combined in whole or in part one with another as the claims and/or art may direct, either directly or indirectly, implicitly or explicitly.

Finally, the fact that the wording "an embodiment," or the like, does not appear at the beginning of every sentence in the specification, such as is the practice of some practitioners, is merely a convenience for the reader's clarity. However, it is the intention of this application to incorporate by reference the phrasing "an embodiment," and the like, at the beginning of every sentence herein where logically possible and appropriate.

The present invention advances prior art skin cleansing articles by providing an article with a skin-protecting and moisturizing compound formulated with fucoidan from seaweed, such as limu moui, kombu, or mozuku. The addition of fucoidan to the article of the present invention serves to provide significant advantages not found in prior art skin protection compositions. The fucoidan-enhanced articles of the present invention provides many beneficial functions, including providing for anti-aging, and regeneration of cells and tissues; promoting youthfulness; reducing inflammation and the like. In addition, the fucoidan-enhanced skin protection compositions of the present invention minimize the visible signs of both biological and environmental aging. That is, the present compositions may slow the aging process, assist in regenerating damaged cells and tissues, and promote growth factors in the body. Fucoidan is high in antioxidants that help to fight free radical damage to the body that may lead to cancer. These antioxidants help to fight free radical damage caused by the sun and other changing environmental conditions and elements.

The present invention includes a skin cleansing article which includes a carrier, and a moist application. The moist application includes partially hydrolyzed fucoidan, and is applied to the carrier. The skin cleansing article may be further formulated to cleanse skin, and leave a residue on the skin that promotes healing of the skin.

The Carrier

The carrier of the present invention may include any of several available forms. The carrier may be a single substrate, or several substrates. The desired use of the skin cleansing article may help in determining the carrier to be used for the skin cleansing article.

As used herein, the term "carrier" includes woven materials, nonwoven materials, foams, sponges, battings, balls, puffs, films, and the like. The nonwoven substrates can comprise any conventionally fashioned nonwoven sheet or web having suitable basis weight, caliper (thickness), absorbency and strength characteristics. Nonwoven substrates can be generally defined as bonded fibrous or filamentous products having a web structure, in which the fibers or filaments are distributed randomly as in "air-laying" or certain "wet-laying" processes, or with a degree of orientation, as in certain "wet-laying" or "carding" processes. The fibers or filaments of such nonwoven substrates can be natural (e.g., wood pulp, wool, silk, jute, hemp, cotton, linen, sisal or ramie) or synthetic (e.g., rayon, cellulose ester, polyvinyl derivatives, polyolefins, polyamides or polyesters) and can be bonded together with a polymeric binder resin. Examples of suitable commercially available nonwoven substrates include those marketed under the tradename Sontara™ by DuPont and Polyweb™ by James River Corp.

In one embodiment, the skin cleansing article of the present invention is capable of being disposed of through plumbing. For example, the skin cleansing article may be flushable. In order for the skin cleansing article to be flushable, the carrier may be nonwoven and formed from wood pulp fibers, i.e., paper webs. As noted, paper webs can be prepared by either air-laying or wet-laying techniques. Air-laid paper webs such as Air Tex™ SC130 are commercially available from James River Corp.

More conventionally, paper webs may be made by wet-laying procedures. In such procedures, a web is made by forming an aqueous papermaking furnish, depositing this furnish onto a foraminous surface, such as a Fourdrinier wire, and by then removing water from the furnish, for example by gravity, by vacuum assisted drying and/or by evaporation, with or without pressing, to thereby form a paper web of desired fiber consistency. In many cases, the papermaking apparatus is set up to rearrange the fibers in the slurry of papermaking furnish as dewatering proceeds in order to form paper substrates of especially desirable strength, hand, bulk, appearance, absorbency, and so forth.

The papermaking furnish utilized to form the paper web substrates for articles of the present invention essentially comprises an aqueous slurry of papermaking fibers (i.e., paper pulp) and can optionally contain a wide variety of chemicals such as wet strength resins, surfactants, pH control agents, softness additives, debonding agents and the like. Wood pulp in all its variations can be used to form the papermaking furnish. Wood pulps useful herein include both sulfite and sulfate pulps, as well as mechanical, thermo-mechanical and chem-thermo-mechanical pulps, all of which are well known to those skilled in the papermaking art. Pulps derived from deciduous and/or coniferous trees can be used. The papermaking furnish used to form the paper web substrates for wipes of the present invention may comprise Kraft pulp derived from northern softwoods.

A number of papermaking processes have been developed which utilize a papermaking apparatus that forms paper webs having particularly useful or desirable fiber configurations. Such configurations can serve to impart such characteristics of the paper web as enhanced bulk, absorbency and strength. One such process employs an imprinting fabric in the papermaking process that serves to impart a knuckle pattern of high density and low density zones into the resulting paper web. A process of this type, and the papermaking apparatus for carrying out this process, is described in greater detail in U.S. Pat. No. 3,301,746 (Sanford et al), issued Jan. 31, 1967, which is incorporated by reference.

In addition to papermaking fibers, the papermaking furnish used to make these paper web substrates can have other components or materials added thereto as can be or later become known in the art. The types of additives desirable will be dependent upon the particular end use of the tissue sheet contemplated. For example, in wipe products such as toilet paper, paper towels, facial tissues, baby wipes and other similar products, high wet strength is a desirable attribute. Thus, it is often desirable to add to the papermaking furnish chemical substances known in the art as "wet strength" resins. The most useful wet strength resins have generally been cationic in character. For permanent wet strength generation, polyamide-epichlorohydrin resins are cationic wet strength resins that have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Del., which markets such resins under the mark Kymene™ 557H.

Polyacrylamide resins have also been found to be of utility as wet strength resins. One commercial source of polyacrylamide resins is American Cyanamid Co. of Stamford, Conn., which markets one such resin under the mark Parez™ 631 NC.

Still other water-soluble cationic resins finding utility as wet strength resins are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins sold under particular tradenames such as Caldas 10 (manufactured by Japan Carlit), CoBond 1000 (manufactured by National Starch and Chemical Company), and Parez 750 (manufactured by American Cyanamide Co.) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing lint of the paper substrate, low levels of starch binders also impart a modest improvement in the dry tensile strength without imparting stiffness that could result from the addition of high levels of starch. Typically the starch binder is included in an amount such that it is retained at a level of from about 0.01 to about 2%, or from about 0.1 to about 1%, by weight of the paper substrate.

In general, suitable starch binders for these paper web substrates are characterized by water solubility, and hydrophilicity. Although it is not intended to limit the scope of suitable starch binders, representative starch materials include corn starch and potato starch, with waxy corn starch known industrially as amioca starch being useful. Amioca starch differs from common corn starch in that it is entirely amylopectin, whereas common corn starch contains both amylopectin and amylose. The starch binder can be in granular or dispersed form, the granular form being useful. The starch binder may be sufficiently cooked to induce swelling of the granules. The starch granules may be swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes.

Due to the necessity for flexability of the wipe article to allow for better cleaning, it is desirable to mechanically treat hydrophobic thin films in such a way as to make them more flexible. Ring-rolling is an option which gives a film more flexibility.

The Moist Application

The moist application may include any application suitable for application to the carrier and which promotes the cleaning and healing of the skin. The application may include a base and partially hydrolyzed fucoidan. The moist application may be a single phase such as a mineral oil, baby oil, vegetable oil, or so forth. The moist application may also include that as disclosed in U.S. Pat. No. 5,980,922 to Mackey, et al (9 Nov. 1999), which is herein incorporated by a reference. Mackey discloses an emulsion comprising a continuous solidified lipid phase, an internal polar phase dispersed in the lipid phase, a non-silicone containing emulsifier, and an optional second emulsifier. The liquid phase of this patent includes a waxy external phase, and the internal phase is retained in the emulsion until in-use shear pressures break the emulsion, providing moisture for cleaning.

1. Bases for the Moist Application

Ideally, a base should be nonirritating, nondehydrating, nongreasy, compatible with active ingredients, stable, easily removable with water, absorptive (able to absorb water and/or other liquids), and able to efficiently release the incorporated active ingredients. Ointments may be classified according to type, based on composition. Such ointment classes include oleaginous bases, absorption bases, emulsion bases, and water-soluble bases.

Oleaginous bases are generally anhydrous, hydrophobic, insoluble in water, and are not water-removable. Oleaginous bases includes the early ointments, which consisted almost entirely of vegetable and animal fats, as well as petroleum hydrocarbons. Fixed oils of vegetable origin include olive, cottonseed, sesame, persic, and other oils. Hydrocarbon bases include ointments prepared from petrolatum or liquid petrolatum with wax or other stiffening agents. Hydrocarbon bases do not become rancid, which is an advantage compared to animal fats and vegetable oils. Another oleaginous base includes silicones, which are synthetic polymers in which the basic structure is an alternating chain of silicon and oxygen atoms (e.g., —O—Si—O—Si—O—Si—). Silicones used in the pharmaceutical and cosmetic industries include dimethylpolysiloxane, methylphenylpolysiloxane, and a stearyl ester of dimethylpolysiloxane, all of which are insoluble in water and are water repellant. Illustrative oleaginous bases are well known in the art, such as Silicone Gibson Base (Example 2) and Vanisil Silicone Ointment (Example 3).

Absorption bases are generally anhydrous, hydrophilic, insoluble in water, and most are not water-removable. These bases have the property of absorbing several times their weight of water and forming emulsions while retaining their ointment-like consistency. Absorption bases vary in their composition, but for the greater part, they are mixtures of animal sterols with petrolatum. Combinations of cholesterol and/or other lanolin fractions with white petrolatum are such absorption bases sold under the tradenames of Eucerin® and Aquaphor® (available from Beirsdorf Aktiengesellschaft Corporation, Germany) were among the earliest commercial bases of this type. Zopf Emollient Cream (Example 4), Hoch Formula (Example 5), Hydrophilic Petrolatum Base (Example 6), Wool Alcohols Base (Example 7), and Aquabase Ointment (Example 8) are absorption bases described herein. Some commercially available absorption bases include those sold under the tradenames Polysorb® (made by Fougera, a division of Altana Inc, Melville, N.Y.), and Nivea® Cream (Made by Duke Laboratories, South Norwalk, Conn.).

Emulsion bases may be either W/O bases, which are hydrous, insoluble in water, and not removable with water and will absorb water, or O/W bases, which are hydrous, insoluble in water, and water-removable and will absorb water. These preparations are solid emulsions, and similar products have long been used as cosmetic creams. The availability of numerous compounds for use as wetting agents, dispersing agents, emulsifiers, penetrants, emollients, detergents, hardeners, preservatives, and the like has given a great deal of flexibility to ointment formulation. Although surface-active agents (i.e., surfactants) may be ionic or nonionic, the nonionic agents are widely used in dermatologic and pharmaceutical preparations. Polysorbate 80 (e.g., Tween 80) and Polyoxyl 40 Stearate represent such surfactants. Nonionic surfactants are generally less toxic and less irritating than ionic surfactants. Other advantages include their virtual neutrality, stability to freezing, stability to electrolytes, and ease of use. In general, the emulsion bases contain an aqueous phase, an emulsifying agent, and an oleaginous phase. The water phase of illustrative emulsion bases typically varies from 10 to 80% by weight of the total base. Glycerin, propylene glycol, or a polyethylene glycol is generally included with the aqueous phase to serve as a humectant, to reduce water loss through evaporation, and to lend a general softness to the creams.

The addition of certain alcohols to emulsion base formulas also adds stability to the emulsion and imparts a smooth feel to the skin. Stearyl alcohol, a solid, increases the consistency of the ointment and permits the incorporation of more liquid components. Due to their ability to become hydrated, such alcohols assist in water retention of emulsion bases. The oleaginous phase may contain one or more of the following or similar ingredients: petrolatum, fats, waxes, organic alcohols, polyglycol esters, or other grease-like substances. These substances are emulsified with the aqueous phase through the action of the surfactant. A few such emulsifiers include alkali soaps, alkyl sulfates, amine soaps, polyglycol esters, alkyl aryl sulfates, quaternary ammonium compounds, and the like. These emulsifying compounds aid in the dispersion of the fats and waxes in water and increase the stability of the ointments. Hydrophilic Ointment Base (Example 11), Beeler's Base (Example 12), and U.C.H. Base (Example 13) are illustrative O/W emulsion bases described herein. Commercially available O/W emulsion bases include those sold under the tradenames of Cetaphil® Cream (made by Galaderma Laboratories, L.P., Princeton, N.J.), Neobase (made by Neobase, Seattle, Wash.), Unibase® (made by Pfizer, New York, N.Y.), Dermovan, Phorsix Cream, Lubriderm® Cream (made by Pfizer, New York, N.Y.), and Velvachol® (available from Galderma Laboratories, Inc., Fort Worth, Tex.).

Water-soluble bases are anhydrous, soluble in water, water-removable, and greaseless, and will absorb water. These bases include those bases prepared from polyethylene glycols as well as semisolid preparations containing bentonite, colloidal magnesium aluminum silicate, and sodium alginate. Polyethylene glycol (PEG) compounds 1500, 1540, 4000, and 6000 are of interest in ointment and lotion formulations. PEG 1500 is a soft waxy solid, similar in consistency to petrolatum, with a congealing range of 40° C. to 45° C. PEG 1540 is a solid of consistency of beeswax and is intermediate in physical properties between the 1500 and 4000 PEGs. PEG 4000 has a congealing range of 53° C. to 56° C. and is most useful as a component of being an ointment base for, in addition to the general property of being an emulsifying and dispersing agent, it also adds to the consistency of the base. Both PEG 4000 and PEG 6000 are nonhygroscopic. PEG 6000 is a hard, translucent, waxy solid, and has a congealing range of 58° C. to 62° C.

Glyceryl monostearate is a polyhydric alcohol ester that has been widely used in cosmetic and ointment bases. It has a high melting point (56° C. to 58° C.) and is a good emulsifying agent. Glyceryl monostearate emulsions generally contain high water phases, usually above 60% by weight. It has the disadvantage of being incompatible with acids. Glyceryl Monostearate Base (Example 23) is described herein.

Cellulose derivatives, such as methylcellulose and hydroxyethyl cellulose, form colloidal solutions that resemble gums and mucilages, but are not as vulnerable to fungal or bacterial attack. Methylcellulose is dispersible in cold water, but in concentrated solutions will coagulate upon heating. Hydroxyethyl cellulose is more soluble at elevated temperatures so that viscosity of aqueous solutions decreases slightly on warming. It is a good protective colloid for aqueous dispersions of oils, waxes, and pigments. Sodium carboxymethylcellulose is another cellulose derivative frequently referred to as carboxymethyl cellulose or CMC. It is an anionic compound and thereby may be used as a thickening or stabilizing agent for suspensions and for ointments of the emulsion type where the emulsifying agent is anionic or nonionic. Any of these cellulose derivatives may be used to stabilize ointment formulas, and they are commercially available in various viscosity types and with various degrees of substitution.

Sodium alginate is a hydrophilic colloid that is compatible with small amounts of alcohol, glycerin, polyglycols, wetting agents, and solutions of alkali carbonates. It functions satisfactorily under acid or alkaline conditions within the pH range of 4.5-10. It is possible to make sodium alginate solutions into semi-firm or firm gels by the addition of small amounts of soluble calcium salts, i.e., calcium gluconate, calcium tartrate, and calcium citrate. Ions of the alkaline earth metals will thicken or gelatinize sodium alginate solutions when present in low concentrations, while at high concentrations they will precipitate them. A 2.5% solution of sodium alginate is a satisfactory inert diluent for greaseless and other types of ointments.

Bentonite, a colloidal hydrated aluminum silicate, is insoluble in water, but when mixed with 8 to 10 parts of water it swells to produce a slightly alkaline gel resembling petrolatum. The consistency of the product may be regulated by varying the amounts of water added. Ointments prepared from bentonite and water alone are found to be slightly drying and unstable upon standing, but addition of a humectant, such as glycerin or sorbitol, in amounts up to about 10% by weight will retard this action. Ointments prepared from bentonite do not encourage mold growth, and they have the advantage of not spreading to the hair when applied to the scalp.

Colloidal magnesium aluminum silicate (e.g., that sold under the tradename of Veegum®, R.T. Vanderbilt Company, Inc.) is an inorganic emulsifier, suspending agent, and thickener. Dispersions are slightly alkaline and are compatible with about 20 to 30% ethyl alcohol, isopropyl alcohol, acetone, and similar solvents. Glycols, such as glycerin and propylene glycol, are compatible at 40 to 50% concentrations.

Acid polymers sold under the tradename Carbopol® 934 (carboxypolymethylene, made by B. F. Goodrich Chemical Co., Akron, Ohio) disperse readily in water to yield an acid solution of low viscosity. When the acid solution is neutralized with a suitable base, such as sodium bicarbonate, sodium hydroxide, or the like, a clear, stable gel results. Carbopol® 934 is inert physiologically and is neither a primary irritant nor a sensitizer. The thickening efficiency of Carbopol® 934 may be used in the preparation of such pharmaceuticals as creams, ointments, lotions, suspensions, and emulsions.

2. Partially Hydrolyzed Fucoidan

The present invention advances prior art skin care compositions by providing a skin care composition formulated with fucoidan from seaweed, such as limu moui, kombu, or mozuku. The addition of fucoidan to the skin care composition of the present invention serves to provide significant advantages not found in prior art skin care compositions. The fucoidan-enhanced skin care articles of the present invention provides many beneficial functions, including providing for anti-aging, and regeneration of cells and tissues; promoting youthfulness; reducing inflammation and the like. In addition, the fucoidan-enhanced skin care articles of the present invention minimize the visible signs of both biological and environmental aging. That is, the present dietary supplements slow the aging process, assist in regenerating damaged cells and tissues, and promote growth factors in the body. Fucoidan is high in antioxidants that help to fight free radical damage to the body that may lead to cancer. These antioxidants help to fight free radical damage caused by the sun and other changing environmental conditions and elements.

Brown seaweed, a source of fucoidan, grows in many oceans, including off the coasts of Japan and Okinawa, Russian coastal waters, Tonga, and other places. An excellent source of fucoidan is the limu moui sea plant growing in the waters of the Tongan islands. This brown seaweed contains many vitamins, minerals, and other beneficial substances and is particularly rich in fucoidan.

Typically, the brown seaweed grows in long angel hair stems with numerous leaves. The fucoidan ingredient is found in natural compositions on the cell walls of the seaweed, providing a slippery sticky texture that protects the cell walls from the sunlight.

In one embodiment, a kombu-type or mozuku-type seaweed is harvested from the coastal waters of the Tongan islands. These seaweeds can be manually harvested, including stems and leaves, by divers and cleaned to remove extraneous materials. The seaweed is then usually frozen in large containers and shipped to a processing plant.

In processing, the heavy outer fibers must first be broken down to provide access to the fucoidan component. If frozen, the seaweed material is first thawed, but if not frozen, then the seaweed material is placed in a mixing vat and shredded, while being hydrolyzed with acids and water. The material may optionally be sulfonated with sulfuric acid to help in breaking down the heavy cell fibers. The mixture is also buffered with citric acid and thoroughly blended to maintain suspension. The material may also be heated at atmospheric or greater than atmospheric pressure while mixing. The resulting puree is tested and maintained at a pH of about 2 to 4 so as to remain acidic, thus enhancing preservative and stability characteristics.

The puree may be used in preparing skin care articles. Alternately, the mixture may be refrozen in small containers for later processing.

According to one embodiment, the present invention provides a skin care composition formulated with fucoidan compositions from seaweed, such as the limu moui seaweed plant, the Japanese mozuku seaweed, or Japanese kombu seaweed, or mixtures thereof. In another embodiment, the fucoidan may be partially hydrolyzed fucoidan. In yet another embodiment, the fucoidan may be sulfonated. In still another embodiment, the fucoidan compositions are present in selected embodiments in the amount of at least about 0.05 weight percent, or at least about 3 weight percent, or at least about 5 weight percent; and less than about 100 weight percent, or less than about 80 weight percent, or less than about 50 weight percent of the total weight of the moist application.

In a further embodiment, the partially hydrolyzed fucoidan may be derived from Tongan limu moui, Japanese hoku kombu (*Laminaria japonica*), wakame, or mozuku (*Cladosiphon* and *Nemacystus*). In still a further embodiment, the partially hydrolyzed fucoidan may be sulfonated.

3. Other Components of the Liquid Phase

Optional components may be included in the skin care article either within the moist application, or separate from the moist application, and also applied to the carrier. These optional components may include, for example, detergents, surfactants, colorants, fragrances, antimicrobials, antiseptics, analgesics, vitamins, botanical extracts, glycolipids, polymers, copolymers, antioxidants, and the like. The Cosmetic, Toiletry, and Fragrance Association's International Cosmetic Ingredient Dictionary and Handbook is an excellent source of information concerning such ingredients.

As used herein, "colorants" or "coloring agents" are agents that give skin care compositions a more pleasing appearance, and in addition help the manufacturer to control the product during its preparation and help the user to identify the product. Any of the approved certified water-soluble FD&C dyes, mixtures thereof, or their corresponding lakes may be used to color skin care compositions. A color lake is the combination by adsorption of a water-soluble dye to a hydrous oxide of a heavy metal, resulting in an insoluble form of the dye.

As to the detergents and surfactants, these may be added to the moist application or directly to the carrier. The detergents and surfactants may include anionic, cationic, non-ionic, zwiterionic, and ampholytic surfactants. Some examples of detergents or surfactants include sodium linear alkylbenzene sulfonates, alkyl athoxy sulfates, alkyl ethoxylates, alkyl amine oxides, alkyl polyglycosides, cetyl trimethyl ammonium salts, lauryl trimethyl ammonium salts, and so forth.

There may also be other natural components added to the carrier or to the moist application. These natural components may include, for example, witch hazel, mangosteen, honey, aloe, sage, piper, clove, ginger, red pepper, willow, rhubarb, sesame, chamomile, propolis, thyme, lavender, cinnamon oil, flower or blossom oils, olive oil, palm oil, coconut oil, beeswax, and so forth. One particularly beneficial natural ingredient is a derivative of the mangosteen plant. According to one embodiment, the present invention includes from about 0.01 to about 10 weight percent of a derivative of the mangosteen plant.

The Mangosteen plant (*Garcinia mangostana* L.) is a tropical fruit-bearing plant named after the French explorer Laurent Garcin. Many of the benefits of the mangosteen plant and its derivatives are descrived in U.S. Pat. No. 6,730,333, which is herein incorporated by a reference. Over the years, the mangosteen plant has been used in a number of different ways. The timber is used for cabinets, building materials, fencing and furniture. The pericarp, containing pectin, tannins, resins and a yellow latex, is used in tanning and dyeing leather black. The fruit pulp is mostly used as a dessert, but can also be canned or made into preserves. However, when removing the fruit pulp from the rind, care must be taken to prevent the tannins and resins of the cut pericarp from contacting the fruit pulp. The mangosteen rind, leaves and bark have also been used as ingredients in folk medicine in areas where the plant grows indigenously. The thick mangosteen rind is used for treating catarrh, cystitis, diarrhea, dysentery, eczema, fever, intestinal ailments, itch, and skin ailments. The mangosteen leaves arc used by some natives in teas and other decoctions for diarrhea, dysentery, fever, and thrush. It is also known that concoctions of mangosteen bark can be used for genitourinary afflictions and stomatosis.

Some of the medicinal properties of the *Garcinia mangostana L.* plant have been the subject of pharmacological and clinical studies. These studies have isolated chemical constituents in the mangosteen leaves, wood, pericarp and seed aril, which were found to contain the following biologically active compounds, among others: 1,6-dihydroxy-3-methoxy-2-(3-methyl-2-butenyl) xanthone, 1,5,8-trihydroxy-3-methoxy-2-(3-methyl-2-butenyl) xanthone, maclurin, 1,3,6,7-tetrahydroxy xanthone, 1,3,6,7-tetrahydroxy xanthone-O-β-D-glucoside, chrysanthemin, cyaniding-3-O-β-D-sophoroside, 8-deoxygartanin, 1,5-dihydroxy-2-isopentenyl-3-methoxy xanthone, 1,7-dihydroxy-2-isopentenyl-3-methoxy xanthone, 5,9-dihydroxy-8-methoxy-2,2-dimethyl-7-(3-methylbut-2-enyl)2(H), 6(H)-pyrano-(3,2,6)-xanthen-6-one, fructose, garcinone A, B, C, D and E, gartanin, glucose, cis-hex-3-enyl acetate, 3-isomangostin, 3-isomangostin hydrate, 1-isomangostin, 1-isomangostin hydrate, kolanone, mangostin, β-mangostin, α-mangostin, mangostin-3,6-di-O-gulcoside, normangostin, sucrose, tannins, BR-xanthone-A, BR-xanthone-B, calabaxanthone demethylcalabaxanthone, 2-(γ,γ-dimethylallyl)-1,7-dihydroxy-3-methoxyxanthone, 2,8-bis-(γ,γ-dimethylallyl)-1,3,7-trihydroxyxanthone, 1,3,5,8-tetrahydroxy-2,4-diprenylxanthone, and mangostanol. Many of these chemical constituents are xanthones, which are biologically active compounds that are receiving increasing interest in pharmacological studies for a variety of health benefits.

The moist application of the present invention can also include topical analgesics agents such as, but not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, arncinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, piroxicam, isoxicam, tenoxicam, sudoxicam, CP-14,304, aspirin, disalcid, benorylate, trilisate, safapryn, solprin, diflunisal, and fendosal, diclofenac, fenclofenac, indomethacin, sulindac, tolmetin, isoxepac, furofenac, tiopinac, zidometacin, acematacin, fentiazac, zomepiract, clidanac, oxepinac, and felbinac, mefenamic, meclofenamic, flufenamic, niflumic, and tolfenamic acid, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic, phenybutezone, oxyphenbutezone, feprazone, azapropezone, and trimethazone and mixtures thereof.

The moist application of the present invention may also include anti-oxidant or radical scavengers. Suitable anti-oxidants or radical scavengers include, but are not limited to, butylated hydroxy benzoic acids, 6-hydroxy-2,5,7,8-tetramethylchroman-2-carboxylic acid, gallic acid, propyl gallate, uric acid, sorbic acid, ascorbyl esters of fatty acids, amines, sulfhydryl compounds, dihydroxy fumaric acid, pharmaceutically acceptable salts thereof, alkyl esters thereof, derivatives thereof and mixtures thereof.

The moist application of the present invention may also include topically administered vitamins. Such vitamins include, but are not limited to Vitamin A, ascorbic acid, Vitamin B, biotin, panthothenic acid, Vitamin D, Vitamin E and mixtures thereof and derivatives thereof. Derivatives or analogs of these vitamins may also be used such as synthetic Vitamin A analogs, natural Vitamin A analogs, geometric isomers and stereoisomers and mixtures thereof.

Barrier Application

According to one embodiment of the present invention, the skin cleansing article includes a barrier application. The barrier application may function so as that when the skin cleansing article is used, the barrier application is left on the skin to guard the skin from waste that may be introduced to, and held next to the skin. Barrier applications may include any of several substances that function to provide a barrier on the skin. The barrier application may be the base, or may be added to the moist application in addition to the base. Alternatively, the barrier application may be added to the surface of the carrier either with the moist application, or on a separate surface, or a separate part of the surface from the moist application. For example, the moist application and the barrier application may be added to a single side of the carrier in alternating strips such that when the skin cleaning article is wiped across skin, the moist application helps to clean the skin, and the following barrier application strip leaves a substance on the skin to protect it from further exposure to waste that may be held next to the skin.

Barrier applications may be chosen according to the function that it must perform, their water repellant properties, their skin conditioning properties, their appearance, their feel, their fragrance, and so forth. Further, consumers are increasingly interested in natural products for topical application. As a result, many barrier applications are available that exhibit good properties in several or all of the areas mentioned.

One typical barrier is zinc oxide. Zinc oxide is widely used for its properties as a barrier application. Zinc oxide is also known to be a barrier material to prevent eczema, excoriations, and so forth. It may be used in a paste or cream, and may be used in combination with other topical actives. Zinc oxide is almost totally insoluble in water.

Another typical barrier is petrolatum. Petrolatum includes petroleum jelly, paraffin jelly, vasoliment, and so forth. It is commonly used as an occlusive barrier material in topical preparations. Petrolatum is generally a purified mixture of semi-solid hydrocarbons of the general formula $C_nH_{2n+2}$, where n is about 16 to about 32. Premium petrolatum is white, semi-solid, unctuous mass which is odorless and tasteless. Petrolatum is sold under the tradename Vaseline® (Chesebrough-Pond's USA Co., Greenwich, Conn.).

Natural barrier applications may also be used. One possible natural barrier application includes derivatives of vegetable oils. Vegetable oils typically exist in liquid form at room temperature, such as, for example, arachis oil, sesame oil, coconut oil, soybean oil, cottonseed oil, palm oil, thistle oil, walnut oil, castor oil, canola oil, olive oil, corn oil, rapeseed oil, linseed oil, safflower oil, peanut oil, almond oil, apricot oil, avocado oil, flax oil, grapeseed oil, hazelnut oil, pine oil, poppy oil, pumpkin oil, rice bran oil, tea oil, wheat oil, cocoa oil, cocoa butter, and so forth. Some vegetable oils, such as olive oil, congeal at just below room temperature.

Animal oils may also be used as the barrier application. Some examples of animal oils include whale oil, cod-liver oil, musk oil or mink oil. Also included in the category of animal oils are oils or fats from milk. For example, cream from milk may be used as the barrier application in the present invention.

In one embodiment, any known process may be used to increase the viscosity of the vegetable oil to a point that it may be an effective barrier application in the present invention. On such process is hydrogenation. Hydrogenation is a process whereby hydrogen is reacted with the vegetable oil such that the unsaturated (double and/or triple) bonds between two carbon atoms are reduced by the addition of hydrogen between the bonds. The result is a fully-hydrogenated (no unsaturated bonds are left) or partially-hydrogenated (some unsaturated bonds are left) vegetable oil. These fully or partially hydrogenated vegetable oils typically become solid at room temperature and slightly above room temperature.

The barrier application may include any of the components that may be added to the liquid phase, such as partially hydrolyzed fucoidan, natural ingredients, analgesics, antioxidants, and any other mentioned above. According to one embodiment, the barrier application includes partially hydrolyzed fucoidan. According to another embodiment, the barrier application includes detergents, surfactants, colorants, fragrances, antimicrobials, antiseptics, analgesics, vitamins, botanical extracts, glycolipids, polymers, copolymers, and the like. There may also by other natural components added to the carrier or to the moist application. These natural components may include, for example, witch hazel, mangosteen, honey, aloe, sage, piper, clove, ginger, red pepper, willow, rhubarb, sesame, chamomile, propolis, thyme, lavender, cinnamon oil, flower or blossom oils, olive oil, palm oil, coconut oil, beeswax, and so forth. One particularly beneficial natural ingredient is a derivative of the mangosteen plant. According to one embodiment, the barrier application includes from about 0.01 to about 10 weight percent of a derivative of the mangosteen plant.

In order to demonstrate the practice of the present invention, the following examples have been prepared. Some of the examples may be labeled as "prophetic." It is assumed that such examples may not have been actually yet performed. The examples should not, however, be viewed as limiting the scope of the invention. The claims will serve to define the invention.

PROPHETIC EXAMPLE 1

Preparation of Fucoidan Puree Composition

Tongan limu moui seaweed is manually harvested, cleaned to remove extraneous material, frozen, and shipped to a processing plant. At the plant, the frozen seaweed is thawed, weighed, and placed in a stainless steel mixer with aqueous buffer and optionally sulfuric acid according to any of the sets of conditions set out in Table 1. The ingredients are then mixed at 50-75 rpm with a medium shear mixer (propeller type). While mixing, the mixture was heated to 37° C. to 95° C. for a selected period of time (usually 5 min to 8 hr). At that point, heating is discontinued, but mixing is continued for 0.5-10 hours to dissipate heat and micronize the seaweed strands. The cooled mixture is then filtered to remove insoluble material, and the filtrate is covered and mixed at room temperature for about 4-72 hours. The pH of the resulting puree is determined to be about pH 2.0 to 4.0, and refractometry typically shows a Brix value of 2-4. The puree comprising partially hydrolyzed fucoidan is then frozen and stored. When sulfuric acid is added during hydrolysis, the partially hydrolyzed fucoidan is sulfonated.

TABLE 1

| | Trial I | Trial II | Trial III | Trial IV | Trial V | Trial VI | Trial VII |
| --- | --- | --- | --- | --- | --- | --- | --- |
| pH | 2.0-2.4 | 2.2-2.5 | 2.4-2.7 | 2.6-3.0 | 2.9-3.2 | 3.2-3.6 | 3.6-4.0 |
| sulfuric acid | — | 0.01 N | — | 0.001 N | 0.004 N | — | 0.001 |
| seaweed | 20 wt % | 10 wt % | 25 wt % | 40 wt % | 33 wt % | 15 wt % | 42 wt % |
| temp | 37 C. | 42 C. | 50 C. | 60 C. | 75 C. | 80 C. | 95 C. |
| heating time | 5 hr | 4 hr | 4 hr | 3 hr | 35 min | 20 min | 15 min |
| filtrate mixing | 24 hr, 37 C. | 16 hr, 37 C. | 72 hr, 22 C. | 24 hr, 22 C. | 48 hr, 22 C. | 36 hr, 22 C. | 8 hr, 22 C. |

PROPHETIC EXAMPLE 2

Silicone Gibson Base

The following formula illustrates a silicone base that may be used in a cream or lotion according to the present invention. Silicone Gibson base comprises 15 parts by weight of cetyl alcohol, 1 parts by weight of sodium lauryl sulfate, 40 parts by weight of dimethylpolysiloxane polymer (1000 cps), 43 parts by weight purified water, 0.25 parts by weight methylparaben, and 0.15 parts by weight propylparaben. The aqueous mixture of the sodium lauryl sulfate and the parabens is warmed to 75° C., and then it is slowly added to warmed (25° C.) cetyl alcohol-silicone mixture. The resulting mixture is stirred until it congeals.

PROPHETIC EXAMPLE 3

Vanisil Silicone Ointment Base

The following formula illustrates a silicone base that may be used in a cream or lotion according to the present invention. Vanisil silicone ointment base comprises 10 parts by weight stearic acid, 2 parts by weight synthetic Japan wax, 20 parts by weight dimethylpolysiloxane polymer (1000 cps), 0.5 parts by weight potassium hydroxide, 0.025 parts by weight methylparaben, 0.015 parts by weight propylparaben, and 67.5 parts by weight distilled water.

PROPHETIC EXAMPLE 4

Zopt Emollient Cream

The following formula illustrates a W/O emulsion absorption base that may be used according to the present invention. Zopf emollient cream comprises 41 parts by weight of white petrolatum, 3 parts by weight of microcrystalline wax, 10 parts by weight of fluid lanolin, 4.75 parts by weight sorbitan monooleate, 0.25 parts by weight of polysorbate 80, and 41 parts by weight purified water. The aqueous dispersion of sorbitan monooleate and polysorbate 80 is warmed to 75° C. and then slowly added to the melted wax, white petrolatum, and fluid lanolin. The resulting mixture is stirred until it congeals.

PROPHETIC EXAMPLE 5

Hoch Formula

The following formula illustrates an O/W emulsion absorption base that may be used according to the present invention. Hoch formula comprises phase A comprising 5 parts by weight of fluid lanolin, 35 parts by weight of castor oil, 2 parts by weight of sorbitan monostearate, 36.7 parts by weight of mineral oil, 4 parts by weight of stearic acid, and 0.2 parts by weight of propylparaben; and phase B comprising 1 parts by weight of polyethylene 20 sorbitan monostearate, 0.9 parts by weight of triethanolamine, 0.2 parts by weight of methylparaben, and 15 parts by weight of purified water. Phase A is heated to 78° C, and phase B is heated to 70° C. Then, phase B is added to phase A and the resulting mixture is stirred until it cools to 25° C.

PROPHETIC EXAMPLE 6

Hydrophilic Petrolatum Base

The following formula illustrates an absorption base that may be used according to the present invention. Hydrophilic petrolatum base comprises 30 parts by weight of cholesterol, 30 parts by weight of stearyl alcohol, 80 parts by weight of white wax, and 860 parts by weight of white petrolatum. The stearyl alcohol, white wax, and white petrolatum are melted together on a steam bath, and then the cholesterol is added and stirred into the mixture until the cholesterol completely dissolves. The mixture is then removed from the bath and stirred until it congeals.

PROPHETIC EXAMPLE 7

Wool Alcohols Base

The following formula illustrates an absorption base that may be used according to the present invention. Wool alcohols ointment base comprises 60 parts by weight wool alcohols, 240 parts by weight hard paraffin, 100 parts by weight white or yellow soft paraffin, and 600 parts by weight liquid paraffin. The ingredients are mixed together and stirred until cold.

PROPHETIC EXAMPLE 8

Aquabase Ointment

The following formula illustrates an absorption base that may be used according to the present invention. Aquabase ointment comprises 30 parts by weight of cholesterol, 30 parts by weight of cottonseed oil, and 940 parts by weight of white petrolatum. The white petrolatum and cottonseed oil are heated to 145° C. and then removed from the heat. The cholesterol is then added and stirred until it is almost congealed. Then the ointment is placed in suitable containers.

PROPHETIC EXAMPLE 9

Emulsion Base

The following formula illustrates an emulsion base that may be used according to the present invention. Many dermatologic and cosmetic preparations contain amine soaps as emulsifying agents. These anionic emulsifiers are advantageous as compared to sodium and potassium soaps because they yield emulsions having a relatively low pH of about 8.0. Triethanolamine is generally used, along with a fatty acid, to produce the fatty acid amine soap. Triethanolamine usually contains small amounts of ethanolamine and diethanolamine. It combines stoichiometrically with fatty acids. Semisolid O/W bases containing triethanolamine soaps are generally prepared by dissolving the triethanolamine in water and then adding this solution to the oil phase with stirring. A typical formula for such a base comprises 18 parts by weight stearic acid, 4 parts by weight of cetyl alcohol, 2 parts by weight of triethanolamine, 5 parts by weight of glycerin, and 71 parts by weight of distilled water.

PROPHETIC EXAMPLE 10

Coal Tar Ointment Base

The following formula illustrates an emulsion base that may be used according to the present invention. Coal tar ointment base contains a surfactant, i.e., polysorbate 80, which serves the dual purpose of a dispersing agent and aiding in removal of the ointment from the skin. Coal tar ointment comprises 10 parts by weight coal tar, 5 parts by weight polysorbate 80, and 985 parts by weight zinc oxide paste. The coal tar is blended with the polysorbate 80, and this blend is then mixed with the zinc oxide paste.

PROPHETIC EXAMPLE 11

Hydrophilic Ointment Base

The following formula illustrates an emulsion base that may be used according to the present invention. Hydrophilic ointment base comprises 0.25 parts by weight methylparaben, 0.15 parts by weight propylparaben, 10 parts by weight sodium lauryl sulfate, 120 parts by weight propylene glycol, 250 parts by weight stearyl alcohol, 250 parts by weight white petrolatum, and 370 parts by weight water. The stearyl alcohol and white petrolatum are melted on a steam bath and warmed to about 75° C. The other ingredients, previously dissolved in the water, are warmed to 75° C. and then added with stirring until the mixture congeals.

PROPHETIC EXAMPLE 12

Beeler's Base

The following formula illustrates an O/W emulsion base that may be used according to the present invention. Beeler's base comprises 15 parts by weight cetyl alcohol, 1 parts by weight white wax, 10 parts by weight propylene glycol, 2 parts by weight sodium lauryl sulfate, and 72 parts by weight water. The cetyl alcohol and white wax are melted in the propylene glycol on a water bath, and the resulting mixture is heated to about 65° C. The sodium lauryl sulfate is dissolved in the water and also heated on water bath to about 65° C. The oil phase is slowly added to the well-stirred water phase, and stirring is continued on the water bath for about 10 min. The emulsion is then removed from the water bath and stirring is continued to the point of congealing.

PROPHETIC EXAMPLE 13

U.C.H. Base

The following formula illustrates an emulsion base that may be used according to the present invention. U.C.H. base comprises 6.4 parts by weight cetyl alcohol, 5.4 parts by weight stearyl alcohol, 1.5 parts by weight sodium lauryl sulfate, 14.3 parts by weight white petrolatum, 21.4 parts by weight mineral oil, and 50 parts by weight water. The alcohols are melted together over a water bath at 65° C., then the sodium lauryl sulfate is add with stirring. Next the white petrolatum and the mineral oil are added with continued heating of the mixture until it is completely melted. This mixture is then cooled to room temperature and the water is added with constant mixing to result in the emulsion.

PROPHETIC EXAMPLE 14

Base A

The following formula illustrates an anhydrous emulsifiable solid mixture. Anhydrous solid mixture A is made by melting together 53 parts by weight of stearyl alcohol, 7 parts by weight of cetyl alcohol, 38.6 parts by weight of PEG 400, and 1.4 parts by weight of sodium lauryl sulfate. These ingredients are melted and stirred vigorously until completely solidified. Stirring is continued to insure complete mixing of the ingredients and for the production of a granular product. Base A is made by melting 50 parts by weight of the granular solid mixture A, heating it to 70-75° C., and then adding it to 50 parts by weight of an aqueous mixture at the same temperature. The mixture is stirred until the emulsion begins to solidify and cools to 40° C. The resulting base is a white, semisolid O/W emulsion of ointment-like consistency. It is non-greasy and washable with water. The emulsion is stable up to 55-60° C., exhibits a good sheen, and exhibits good lubricity when applied to skin.

PROPHETIC EXAMPLE 15

Base B

The following formula illustrates an anhydrous emulsifiable solid mixture. Anhydrous solid mixture B is made by melting together 64.7 parts by weight of stearyl alcohol, 8.6 parts by weight of cetyl alcohol, 13 parts by weight of PEG 1000 monostearate, 8.7 parts by weight of PEG 1540, and 5 parts by weight of anhydrous lanolin. These ingredients are melted and stirred vigorously until completely solidified. Stirring is continued to insure complete mixing of the ingredients and for the production of a granular product. Base B is made by melting 40 parts by weight of the granular solid mixture B, heating it to 70-75° C., and then adding it to 60 parts by weight of an aqueous mixture at the same temperature. The mixture is stirred until the emulsion begins to solidify and cools to 40° C. The resulting base is a white, semisolid O/W emulsion of ointment-like consistency. It is non-greasy and washable with water. The emulsion is stable up to 55-60° C. and exhibits good lubricity when applied to skin.

PROPHETIC EXAMPLE 16

Aqueous Cream Base

The following formula illustrates an emulsion base that may be used according to the present invention. Aqueous cream base is an emulsion base prepared from 30% by weight of emulsifying ointment and 70% by weight of water. Emulsifying ointment comprises 30 parts by weight emulsifying wax, 20 parts by weight liquid paraffin, and 50 parts by weight white soft paraffin. Emulsifying wax comprises 90 parts by weight cetostearyl alcohol, 10 parts by weight sodium lauryl sulfate, and 4 parts by weight purified water.

PROPHETIC EXAMPLE 17

Polyethylene Glycol Ointment Base

The following formula illustrates a water-soluble base that may be used according to the present invention. Polyethylene glycol ointment base comprises 400 parts by weight of PEG 4000 and 600 parts by weight of PEG 400. The two ingredients are heated on a water bath to 65° C., and then the mixture is allowed to cool with stirring until it congeals. If a firmer preparation is desired, up to 100 parts by weight of the PEG 400 may be replaced with an equal amount of PEG 4000. If 6-25% by weight of an aqueous solution is to incorporated in this polyethylene ointment, 50 parts by weight of the PEG 4000 is replaced with an equal amount of stearyl alcohol.

PROPHETIC EXAMPLE 18

Base G

The following formula illustrates a water-soluble base that may be used according to the present invention. The addition of an ester of polyethylene glycol to a polyethylene glycol ointment yields a water-removable, emulsifiable ointment base. An illustrative emulsifiable glycol ointment base (Base G) of this type comprises 26 parts by weight polyethylene glycol 400 monostearate, 37 parts by weight PEG 400, and 37 parts by weight PEG 4000. The glycols are mixed and melted at about 65° C. This mixture is then stirred while cooling to about 40° C. The polyethylene glycol 400 monostearate is melted at about 40° C. and then added to the liquid glycol mixture with stirring until a uniform ointment is obtained. Water (10-15% by weight) may be incorporated into Base G.

PROPHETIC EXAMPLE 19

Base III

The following formula illustrates a water-soluble base that may be used according to the present invention. Surfactants and water may be added to a polyethylene glycol ointment without impairing the water removability of the base. Base III represents a typical formula of this type: 50 parts by weight PEG 4000, 40 parts by weight PEG 400, 1 parts by weight sorbitan monopalmitate, and 9 parts by weight water. The sorbitan monopalmitate and the polyethylene glycols are warmed together on a water bath to 70° C. and the water heated to the same temperature is then added. The emulsion is stirred until it congeals.

PROPHETIC EXAMPLE 20

Modified Landon-Zopf Base

The following formula illustrates a water-soluble base that may be used according to the present invention. Modified Landon-Zopf base comprises 20 parts by weight PEG 4000, 34 parts by weight stearyl alcohol, 30 parts by weight glycerin, 15 parts by weight water, and 1 parts by weight sodium lauryl sulfate. The PEG 4000, stearyl alcohol, and glycerin are heated on a water bath to 75° C. This mixture is then added in small quantities with stirring to the water, which contains the sodium lauryl sulfate and has also been heated to 75° C. Moderate stirring is continued until the base has congealed.

PROPHETIC EXAMPLE 21

Canadian Base

The following formula illustrates a water-soluble base that may be used according to the present invention. Canadian base comprises 11.2 parts by weight PEG 4000, 20.8 parts by weight stearyl alcohol, 17 parts by weight glycerin, 0.6 parts by weight sodium lauryl sulfate, and 50.4 parts by weight water. The PEG 4000, stearyl alcohol, and glycerin are heated on a water bath to 70° C. The water, which contains the sodium lauryl sulfate and has been previously heated to 70° C., is added and the mixture is stirred until the base congeals.

PROPHETIC EXAMPLE 22

Base IV

The following formula illustrates a water-soluble base that may be used according to the present invention. Base IV comprises 42.5 parts by weight PEG 4000, 37.5 parts by weight PEG 400, and 20 parts by weight 1,2,6-hexanetriol. The PEG 4000 is heated with the 1,2,6-hexanetriol is heated on a water bath to 60-70° C. This mixture is added to the PEG 400 at room temperature with vigorous stirring. The, occasional stirring is continued until solidification takes place.

PROPHETIC EXAMPLE 23

Glyceryl Monostearate Base

The following formula illustrates a water-soluble base that may be used according to the present invention. Glyceryl monostearate base comprises 10 parts by weight mineral oil, 30 parts by weight white petrolatum, 10 parts by weight glyceryl monostearate S. E., 5 parts by weight cetyl alcohol, 5 parts by weight glycerin, and 40 parts by weight water.

PROPHETIC EXAMPLE 24

Lubricating Jelly Base

The following formula illustrates a water-soluble base that may be used according to the present invention. Lubricating jelly base comprises 1 g methocel 90 HC 4000, 0.3 g Carbopol® 934, sodium hydroxide as pH 7.0, 20 ml propylene glycol, 0.15 g methylparaben, and purified water as 100 parts by weight. The methocel is added slowly to 40 ml of hot water (80-90° C.) and agitated for 5 min. After cooling, the solution is refrigerated overnight. The Carbopol® 934 is dissolved in 20 ml of water, and 1% sodium hydroxide is added slowly with cautious stirring to avoid incorporation of air, until a pH of 7.0 is obtained, and then water is added to a total volume of 40 ml. The methylparaben is dissolved in the propylene glycol. Finally the methocel, Carbopol®, and methylparaben solutions are mixed cautiously to avoid incorporation of air.

PROPHETIC EXAMPLE 25

Universal O/W Ointment Base

The following formula illustrates a water-soluble base that may be used according to the present invention. Universal O/W ointment base comprises 0.05 parts by weight calcium citrate, 3 parts by weight sodium alginate, 0.20 parts by weight methylparaben, 45 parts by weight glycerin, and sufficient distilled water to make a total of 100 parts by weight. The calcium citrate and the methylparaben are dissolved in the water. The glycerin is mixed with the sodium alginate to form a smooth paste. The aqueous mixture is added to the paste and is stirred until a smooth, stiff preparation is obtained. The base is then set aside for several hours until thickening is complete.

PROPHETIC EXAMPLE 26

Hollander and McClanahan Base

The following formula illustrates a water-soluble base that may be used according to the present invention. Hollander and McClanahan base comprises 32 parts by weight petrolatum, 13 parts by weight bentonite, 0.5 parts by weight sodium lauryl sulfate, 54 parts by weight water, and 0.1 parts by weight methylparaben.

PROPHETIC EXAMPLE 27

MGH Ointment Base

The following formula illustrates a water-soluble base that may be used according to the present invention. MGH ointment base comprises 15 parts by weight polyethylene glycol 200 monostearate, 2.5 parts by weight colloidal magnesium stearate silicate (Veegum), 1 part by weight polysorbate 80, 0.1 parts by weight methylparaben, and 81.4 parts by weight purified water.

PROPHETIC EXAMPLE 28

Lotion Base

The following formula illustrates a water-soluble base that may be used according to the present invention. Lotion base comprises 1 part by weight Veegum, 0.85 parts by weight sodium carboxymethylcellulose, 90.15 parts by weight water, 3 parts by weight glycerin, and 5 parts by weight dioctyl sodium sulfosuccinate (1% solution). All the dry ingredients are mixed with water and glycerin in a blender for 1 min. The mixture is then removed from the blender and the dioctyl sodium sulfosuccinate is added.

PROPHETIC EXAMPLE 29

Cold Cream Base

The following formula illustrates a cold cream according to an embodiment of the present invention. A cold cream base comprises 6 parts by weight spermaceti, 6 parts by weight beeswax, 10 parts by weight Carbopol® 934, 4.75 parts by weight sodium carbonate, 5 parts by weight rose water, 0.02 parts by weight rose oil, 56 parts by weight expressed almond oil, and 20 parts by weight distilled water.

PROPHETIC EXAMPLE 30

Hand Lotion Base

The following formula illustrates a hand lotion according to an embodiment of the present invention. A hand lotion base comprises 24.75 ml propylene glycol, 1 ml triethanolamine, 12 ml water, 1.5 g oleic acid, 10.5 g polyethylene glycol 400 monostearate, 10 ml silicone fluid D.C. 200, and 50 g Carbopol® 934 2% mucilage.

PROPHETIC EXAMPLE 31

White Lotion Base

The following formula illustrates a hand lotion according to an embodiment of the present invention. White lotion base comprises 40 parts by weight zinc sulfate, 40 parts by weight sulfurated potash, and sufficient purified water to make 1000 parts by weight. The zinc sulfate and the sulfurated potash are dissolved separately, each in 450 parts by weight of purified water, and then each solution is filtered. The sulfurated potash solution is then added slowly to the zinc sulfate solution with constant stirring. Then the remainder of the water is added, and the lotion is mixed.

Thus, while the present invention has been fully described above with particularity and detail in connection with what is presently deemed to be the most practical embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A skin cleansing article for cleansing and healing of skin comprising a carrier; a barrier application comprising zinc oxide and partially hydrolyzed sulfonated fucoidan, and a moist application comprising an analgesic and partially hydrolyzed sulfonated fucoidan, wherein the carrier comprises a surface wherein, and the barrier application and the moist application are disposed on a single side of the carrier surface in alternating strips.

2. The skin cleansing article of claim 1, wherein the partially hydrolyzed fucoidan is derived from a seaweed selected from the group consisting of: Japanese mozuku seaweed, Japanese kombu seaweed, Tongan limu moui seaweed, and combinations thereof.

3. The skin cleansing article of claim 1, wherein the moist application includes from about 10 to about 99 weight percent of said fucoidan.

4. The skin cleansing article of claim 1, wherein the moist application further comprises a mangosteen extract.

5. The skin cleansing article of claim 1, wherein the moist application further comprises honey.

* * * * *

UNITED STATES PATENT AND TRADEMARK OFFICE
CERTIFICATE OF CORRECTION

PATENT NO. : 7,666,448 B2
APPLICATION NO. : 11/307034
DATED : February 23, 2010
INVENTOR(S) : Thomas E. Mower It is certified that error appears in the above-identified patent and that said Letters Patent is hereby corrected as shown below:

Column 17, line 24, "descrived" should read --described--.
Column 28, line 29, "surface wherein, and" should read --surface, and wherein--.

Signed and Sealed this

First Day of June, 2010

David J. Kappos
*Director of the United States Patent and Trademark Office*